United States Patent [19]

Yoshino et al.

[11] Patent Number: 4,879,339

[45] Date of Patent: Nov. 7, 1989

[54] STORAGE STABLE AND ROOM TEMPERATURE-CURABLE ORGANOPOLYSILOXANE COMPOSITION

[75] Inventors: Masachika Yoshino, Annaka, Japan; Nobuyuki Hasebe, Rancho Palos Verdes, Calif.; Hironao Fujiki; Hiroshi Inomata, both of Takasaki, Japan

[73] Assignee: Shin-Etsu Chemical Co., Ltd., Tokyo, Japan

[21] Appl. No.: 163,434

[22] Filed: Mar. 3, 1988

[30] Foreign Application Priority Data

Mar. 4, 1987 [JP] Japan .................................. 62-49184

[51] Int. Cl.$^4$ .......................... C08L 5/13; C08L 83/04
[52] U.S. Cl. .................................... 524/740; 524/741; 524/751; 524/752; 524/773; 528/15; 528/31; 528/32; 525/478
[58] Field of Search ............... 524/862, 740, 741, 773, 524/751, 752, 736; 528/15, 18, 31, 32; 525/478

[56] References Cited

U.S. PATENT DOCUMENTS

| 4,035,453 | 7/1977 | Hittmair et al. ...................... 528/15 |
| 4,214,000 | 7/1980 | Papa ..................................... 514/787 |
| 4,273,902 | 6/1981 | Tomioka et al. ...................... 528/15 |
| 4,359,565 | 11/1982 | Puppe et al. .......................... 528/15 |
| 4,568,707 | 2/1986 | Voigt et al. .......................... 524/862 |
| 4,614,758 | 9/1986 | Schwabe et al. ..................... 524/862 |

OTHER PUBLICATIONS

Solomons, T. W. G., "Organic Chemistry", N.Y., J. Wiley & Sons, 1980, pp. 229–232.
Ritchie, P. D., Plasticisers, Stabilisers and Fillers, London, Iliffe Books Ltd., 1972, pp. 246–247.

Primary Examiner—Wilbert J. Briggs, Sr.
Assistant Examiner—R. Dean, Jr.
Attorney, Agent, or Firm—Millen, White & Zelano

[57] ABSTRACT

A room temperature-curable organopolysiloxane composition is proposed which is useful as a material for imprinting or blocking of forms of, for example, medical and dental prostheses without the problem of curing retardation or incomplete curing. The composition comprises a vinyl-containing organopolysiloxane, organohydrogenpolysiloxane, platinum catalyst, inorganic filler, liquid paraffin or petrolatum and antioxidant. The antioxidant serves to protect the liquid paraffin or petrolatum from oxidation to produce oxidized compounds which may deactivate the platinum catalyst to cause curing retardation or incomplete curing.

7 Claims, No Drawings

STORAGE STABLE AND ROOM TEMPERATURE-CURABLE ORGANOPOLYSILOXANE COMPOSITION

BACKGROUND OF THE INVENTION

The present invention relates to a room temperature-curable organopolysiloxane composition, more particularly, to a room temperature-curable organopolysiloxane compostion suitable for use as a material for imprinting or blocking of form which lacks problem of retardation of curing rate or incomplete curing, even after prolonged storage at an elevated temperature.

Among various types of room temperature-curable organopolysiloxane compositions known in the prior art, those used as a material for imprinting or blocking of form are mainly of the type in which curing of the composition proceeds by the addition reaction between an organopolysiloxane having vinyl groups bonded to the silicon atoms and an organohydrogenpolysiloxane having hydrogen atoms directly bonded to the silicon atoms in the presence of a platinum compound as a catalyst.

The room temperature-curable organopolysiloxane composition of the above mentioned type is usually supplied in two packages each of which has a different content and is storable with stability from the other and the contents of the two packages are mixed together directly before use to complete a curable composition. For example, the content of one of the two packages contains the organopolysiloxane having vinyl groups while the content of the other package contains the organohydrogenpolysiloxane. It is a usual formulation with an object to facilitate mixing and handling of the composition by reducing stickiness of the composition under mixing on to the mixing tools and handling fingers that either one or both of the contents are admixed with an internal releasing agent which may be typically an aliphatic hydrocarbon compound having a consistency of a liquid or semi-solid at room temperature such as liquid paraffins and petrolatums.

A problem in such a formulation having an aliphatic hydrocarbon compound as an internal releasing agent in the composition is that the additive compound is susceptible to catalyic oxidation in the presence of a platinum compound as the catalyst for the addition reaction or by the activity of certain active groups on the surface of the inorganic filler particles conventionally added to the composition to produce various oxidized compounds such as carboxylic acids, aldehydes, hydroperoxides and the like which in turn may at least partially deactivate the platinum catalyst so as to cause problems such as curing retardation or incomplete curing when the room temperature-curable organopolysiloxane composition is to be cured.

Retardation in curing rate is a particularly serious problem when the room temperature-curable organopolysiloxane composition is used as a material for imprinting or blocking in dental or medical applications such as preparation of a mold for artificial teeth or for an insert in an external auditory canal because, while, in such an application, the curable composition prepared by uniformly mixing the contents of the two packages taking 20 to 60 seconds and applied to the part of the human body is required to be fully cured within, for example, 3 to 5 minutes before the cured composition is removed from the body. The patient under treatment, who is compelled to remain motionless until full curing of the composition, is subjected to excessive pain by the retardation in curing rate.

In view of the sometimes lengthy marketing route of the products of this kind, which not infrequently exceeds a half year to two years before the product is received by a consumer, a formulation of the room temperature-curable organopolysiloxane composition of this type which is free from the problem of curing retardation or incomplete curing even after prolonged storage is much desired since otherwise the product must be stored at low temperatures or in a hermetically sealed container filled with an inert gas such as nitrogen, which causes great inconveniences and economical disadvantages.

OBJECT OF THE INVENTION

The present invention accordingly has an object to provide a putty-like or pasty room temperature-curable organopolysiloxane composition suitable for use an a material of imprinting or form blocking free from the above described problems and disadvantages in the prior art compositions of the similar type.

SUMMARY OF THE INVENTION

In one aspect the room temperature-curable organopolysiloxane composition of the present invention comprises, in admixture:
(A) 100 parts by weight of an organopolysiloxane having a viscosity of at least 50 centipoise at 25° C. and at least two vinyl groups bonded to the silicon atoms in a molecule;
(B) an organohydrogenpolysiloxane having at least three hydrogen atoms directly bonded to the silicon atoms in a molecule in an amount sufficient to provide from 0.5 to 4.0 moles of the siliconbonded hydrogen atoms per mole of the vinyl groups bonded to the silicon atoms in the component (A);
(C) a catalytic amount of a platinum compound;
(D) from 20 to 600 parts by weight of an inorganic filler;
(E) from 5 to 80 parts by weight of an aliphatic hydrocarbon compound which is liquid or semi-solid at room temperature; and
(F) an antioxidant in an amount of at least 10 ppm by weight based on the aliphatic hydrocarbon compound as the component (E).

In another aspect ths invention relates to a storage-stable organopolysiloxane composition comprising separate first and second portions which, when mixed together at room temperature, rapidly cure into a solid organopolysiloxane composition, wherein I. the first portion is catalyst-free and comprises:
(A) a vinyl group-containing organopolysiloxane which is room temperature curable, in the presence of a reaction catalyst, to a solid organopolysiloxane when in admixture with a cross-linkable organohydrogenpolysiloxane;
(B) an amount of an organohydrogenpolysiloxane having a plurality of hydrogen atoms bonded to the silicon atoms thereof which is room temperature. curable, in the presence of a reaction catalyst with (A), effective to produce the solid organohydrogenpolysiloxane;
(D) inorganic filler;
(E) a liquid or semi-solid aliphatic hydrocarbon release agent; and II. the second portion being free of (B) and containing (A), (D), and (E) as defined hereinabove, a catalyst effective to rapidly convert the first and second portions into a solid organohydrogenpolysiloxane when mixed together at room temperature, the improvement wherein at least the second portion contains (F) an amount of an antioxidant effective to inhibit the oxidation of (E) therein during storage and thereby inhibiting retardation of curing rate or incomplete curing rate of the composition after storage.

DETAILED DESCRIPTION OF THE PREFERRED EMBODIMENTS

The above described room temperature-curable organopolysiloxane composition of the invention is characterized by the formulation of the components (E) and (F) in addition to the rather conventional components (A) to (D). While the admixture of the aliphatic hydrocarbon compound as the component (E) is effective to facilitate the mixing work and handling of the composition, the antioxidant as the component (F) is effective to protect the aliphatic hydrocarbon compound from oxidation to produce various oxidized compounds which are responsible for the deactivation of the platinum catalyst as the component (C), thereby solving the problems of curing retardation or incomplete curing of the composition, even after prolonged storage.

The component (A) as the base ingredient of the inventive composition is an organopolysiloxane having a viscosity of at least 50 centipise at 25° C. and at least two vinyl groups bonded to the silicon atoms in a molecule. Such an organopolysiloxane can be represented by the average unit formula $$Vi_a R_b SiO_{(4-a-b)/2},$$

in which Vi is a vinyl group, R is an optionally substituted monovalent hydrocarbon group free from aliphatic unsaturation exemplified by alkyl groups, e.g., methyl, ethyl, propyl and butyl groups, aryl groups, e.g., phenyl and tolyl groups, aralkyl groups, e.g., benzyl and 2-phenylethyl groups, and cycloalkyl groups, e.g., cyclohexyl group, as well as substituted monovalent hydrocarbon groups with, for example, halogen atoms as the substituents for a part or all of the hydrogen atoms in the above named hydrocarbon groups such as chloromethyl and 3,3,3-trifluoropropyl groups. The subscript a is a positive number in the range from 0.001 to 0.3 and the subscript b is a positive number in the range from 1.8 to 2.5 with the proviso that a +b is in the range from 1.9 to 2.6. Preferably, the organopolysiloxane is a diorganopolysiloxane having a linear molecular structure of which each of the terminal silicon atoms has one or more of vinyl groups bonded thereto although any silicon atoms in the molecular chain may have a vinyl group bonded thereto. It is also preferable that at least 50% by moles of the groups denoted by R in a molecule are methyl groups.

The component (B) is an organohydrogenpolysiloxane which can be represented by the average unit formula $$R_c H_d SiO_{(4-c-d)/2},$$

in which R has the same meansing as defined above, or preferably, R is a methyl group and the subscript c is a positive number in the range from 0.5 to 2.5 and the subscript d is a positive number in the range from 0.015 to 2.0 with the proviso that c+d is in the range fro 1.5 to 2.6. It is important that the organohydrogenpolysiloxane as the component (B) has good miscibility with the organopolysiloxane as the compoinent (A) since the function of the organohydrogenpolysiloxane is to serve as a crosslinking agent of the organopolysiloxane. In this regard, the organohydrogenpolysiloxane should preferably have a molecular weight smaller than that of the organopolysiloxane though not particularly limitative. The amount of the component (B) in the inventive composition is sufficient to provide from 0.5 to 4.0 moles or, preferably, from 1.0 to 3.0 moles of the silicon-bonded hydrogen atoms per mole of the vinyl groups bonded to the silicon atoms in the organopolysiloxane as the component (A). When the amount of the organohydrogenpolysiloxane is too small, the composition is poorly curable due to the deficiency in the crosslinking agent. When the amount thereof is too large, on the other hand, the organopolysiloxane after curing may have brittleness due to the excessively high crossliking density or the cured composition may be subject to changes in mechanical properties over the lapse of time due to the residual amount of the silicon-bonded hydrogen atoms.

The component (C) in the inventive composition is a platinum compound which serves as a catalyst to promote the addition reaction between the silicon-bonded vinyl groups in the component (A) and the silcon-bonded hydrogen atoms in the component (B). The platinum compound is preferably miscible with the components (A) and (B). A suitable platinum compound is chloroplatinic acid which may be used either as such or in the form of an alcoholic solution or a complex with an olefin or vinylsiloxane. The amount of the platinum compound in the inventive composition is the socalled catalytic amount and not particularly limitative depending on the desired curing velocity. As a rough measure, the amount is in the range from 0.0001 to 0.1% by weight as platinum based on the total amount of the components (A) and (B).

The component (D) is an inorganic filler which may be in a fine powdery form or in a fibrous form. Various kinds of known inorganic fillers conventionally used in organopolysiloxane compositions can be used in the inventive composition, including finely divided silica powders, e.g., fumed silica and precipitated silica, quartz powder, glass fibers, carbon powder, iron oxide, titanium dioxide, zinc oxide, calcium carbonate, magnesium carbonate and the like. The amount of the inorganic filler as the component (D) in the inventive composition is in the range, usually, from 20 to 600 parts by weight or, preferably, from 100 to 500 parts by weight per 100 parts by weight of the component (A). When the amount of the inorganic filler is too small, the consistency of the pasty composition is too low with flowability which causes difficulties in handling and, moreover, the aliphatic hydrocarbon compound as the component (E) described below may separate from the composition and float thereon, thus decreasing its effect of facilitating the mixing work of the composition. When the amount thereof is too large, on the other hand, the putty-like composition may be too hard with some crumbliness, which can cause troubles in the imprinting and form-blocking works therewith.

The component (E) is an aliphatic hydrocarbon compound which is liquid, preferably having a viscosity of at least 50 centipoise at 25° C., or semi-solid at room temperature. This component serves to facilitate the mixing of the components to form the inventive composition by imparting releasability to or decreasing the stickiness of the composition. Accordingly, it is important that the aliphatic hydrocarbon compound is at most poorly miscible with the organopolysiloxane as the component (A). Suitable aliphatic hydrocabon compounds include liquid paraffins and petrolatums. The amount of the component (E) is the inventive composition is in the range, usually, from 5 to 80 parts by weight or, preferably, from 15 to 60 parts by weight per 100 parts by weight of the coponent (A). When the amount thereof is too small, insufficient releasability can be imparted to the composition. When the amount thereof is too large, on the other hand, bleeding of the compound onto the surface of the composition may take place.

The component (F) in the inventive composition is an antioxidant which serves to protect the above described aliphatic hydrocarbon compound from oxidation in the presence of the platinum catalyst or by the catalytic activity of certain active groups on the surface of the inorganic filler particles. It is of course important that the antioxidant does not act as a catalyst poison against the platinum compound as the catalyst to promote the addition reaction between the vinyl-containing organopolysiloxane and the organohydrogenpolysiloxane. In this regard, the antioxidant as the component (F) is selected preferably from the group consisting of erythorbic acid, sodium erythorbate, BHT, i.e. 2,6-di-tert-butyl p-cresol, vitamin E, i.e. tocopherol, butyl hydroxy anisole, propyl gallate and the like.

The appropriate amount of the antioxidant as the component (F) in the inventive composition depends on the amount of the aliphatic hydrocarbon compound as the component (E) since the object of formulating this component is to protect the aliphatic hydrocarbon compound from oxidation. Certain effects of oxidation prevention can be exhibited when the amount of the antioxidant is 10 ppm by weight or larger based on the amount of the aliphatic hydrocarbon compound. The amount, however, should preferably be in the range from 100 to 50000 ppm on the same weight basis.

The room temperature-curable organopolysiloxane composition of the invention can be prepared by uniformly mixing together the above described components (A) to (F) each in a calculated and weighed amount. The composition usually has a pasty or putty-like consistency. Since the curing reaction of the thus prepared composition proceeds even at room temperature, the composition is usually prepared in two packages each having a different content from the other and the contents of the two packages are mixed together directly before use. A preferable principle of the two-package formulation of the composition is that the first package, i.e. mixed paste I, contains the components (A) and (C) but does not contain the component (B) and the second package, i.e. mixed paste II, contains the components (A) and (B) but does not contain the component (C). The other essential components, i.e. components (D), (E) and (F), can be contained in either one or both of the mixed pastes I and II as desired. It is of course optional that the inventive composition is further admixed with various kinds of known additives conventionally used in the organopolysiloxane compositions of similar types including moderating agents for the activity of the platinum catalyst such as various nitrogen-containing organic compounds, organophosphorus compounds and acetylene compounds, coloring agents, i.e. dyes and pigments, perfumes and the like according to need.

By virtue of the above described unique formulation of the composition including the combination of the components (E) and (F), the inventive room temperature-curable composition can be prepared very easily by mixing the above mentioned two mixed pastes I and II as a result of copounding of the aliphatic hydrocarbon compound as the component (E). The ready-mixed pastes I and II can be stably stored for prolonged periods of time, even in an atmosphere of open air without causing troubles of curing retardation or incomplete curing because the antioxidant as the component (F) serves to protect the component (E) from oxidation to produce oxidized compounds such as carboxylic acids, aldehydes and the like which may act as a poison against the platinum catalyst, thereby decreasing to decrease the catalytic activity thereof. Accordingly, the inventive composition is useful as a material for imprinting or blocking of teeth forms and inserts of external auditory canals, criminal identification, electric insulation, and so on.

In the following examples, the room temperature-curable organopolysiloxane composition of the present invention is described in more detail by way of examples, in which the term of "parts" always refers to "parts by weight" and the values of viscosity are all those obtained by the measurement at 25° C.

EXAMPLES 1 TO 5 AND COMPARATIVE EXAMPLE 1.

In Comparative Example 1, mixed pastes $I_0$ and $II_0$ were prepared each by uniformly mixing:

80 parts or 75 parts, respectively, of a dimethylpolysiloxane fluid having a viscosity of 2500 centipoise and terminated at each molecular chain end with a dimethyl vinyl siloxy group, the content of the vinyl groups therein being 0.0087 mole per 100 g;

20 parts of a gum-like dimethylpolysiloxane having a viscosity of about 1,000,000 centipoise and terminated at each molecular chain end with a dimethyl vinyl siloxy group, the content of the vinyl groups therein being 0.012% by moles based on overall monovalent hydrocarbon groups;

no parts (mixed paste $I_0$) or 5 parts of (mixed paste $II_0$) methylhydrogen polysiloxane having a viscosity of 12 centipoise and containing 33% bymoles of methyl hydrogen siloxane units, the balance being dimethyl siloxane units and two dimethyl hydrogen siloxy groups at the molecular chain terminals;

0.7 part of (mixed past $I_0$) or no (mixed paste $II_0$) octyl alcohol solution of chloroplatinic acid in a concentration of 1% by weight as platinum;

190 parts of a finely pulverized quartz powder having an average particle diameter of 4 μm;

20 parts of diatomaceous earth having an average particle diameter of 2 μm; and 40 parts of liquid paraffin having a viscosity of 140 centipoise and a specific gravity of 0.88.

In Examples 1 to 5, mixed pastes $I_1$ to $I_5$ and mixed pastes $II_1$ to $II_5$, respectively, were prepared each in the same formulation as in the preparation of the mixed pastes $I_0$ and $II_0$, respectively, described above excepting further admixing of an antioxidant. The kind and the amount of the antioxidant in each Example were as follows:

0.04 part of BHT in each of the mixed pastes $I_1$hd 1 and $II_1$ (Example 1);

0.04 part of butyl hydroxy anisole in each of the mixed pastes $I_2$ and $II_2$ (Example 2);

0.04 part of vitamin E in each of the mixed pastes $I_3$ and $II_3$ (Example 3);

0.02 part of vitamin E in each of the mixed pastes $I_4$ and $II_4$ (Example 4); and 0.2 part of vitamin E in each of the mixed pastes I$_5$ and II$_5$ (Example 5).

In each of the Examples and Comparative Example, the mixed paste I$_0$, etc. and the mixed paste II$_0$, etc. were taken in equal amounts by weight and mixed together manually with a hand using a polyethylene-made glove to give a uniform curable composition, which is referred to as the composition C1 (Comparative Example 1), or composition 1 (Example 1) to composition 5 (Example 5), respectively, hereinbelow. Each of the thus prepared compositions was kept standing at 25° C. in an atmosphere of open air to determine the pot life in seconds to cause loss of plastic deformability. Further, each of the compositions was subjected to curing at room temperature and the hardness, JIS A, of the cured composition was determined after 5 minutes and 30 minutes of curing at 25° C. according to the procedure specified in JIS K 6301 to give the results shown in the table given below.

Separately, each of the mixed pastes I$_0$ to I$_5$ and II$_0$ to II$_5$ was subjected to accelerated aging by keeping at 80° C. for 7 days before mixing together and thereafter the pot life of the ready-mixed composition and the hardness of the cured composition were determined in the same manner as above. The results are also shown in the same table.

The results shown in the table clearly indicate that the addition of the antioxidant was so effective that the curability of the composition was little affected by the accelerated aging while the composition C1 in the comparative example without antioxidant was greatly influenced by aging to show great curing retardation or to lose curability. About the same results as in the above mentioned accelerated aging test could be obtained also in the storage test in which 1 kg each of the mixed pastes were stored in a sealed polyethylene film bag for 6 months including a summer season followed by the same test of the pot life and hardness.

TABLE

| Composition No. | C1 | 1 | 2 | 3 | 4 | 5 |
| --- | --- | --- | --- | --- | --- | --- |
| As prepared | | | | | | |
| Pot life, seconds | 37 | 36 | 36 | 35 | 38 | 37 |
| Hardness, 5 minutes curing | 17 | 15 | 17 | 13 | 15 | 16 |
| Hardness, 30 minutes curing | 56 | 57 | 54 | 55 | 57 | 59 |
| After aging | | | | | | |
| Pot life, seconds | 300 | 38 | 37 | 36 | 37 | 39 |
| Hardness, 5 minutes curing | 0 | 13 | 12 | 15 | 10 | 14 |
| Hardness, 30 minutes curing | 1 | 54 | 58 | 55 | 53 | 57 |

What is claimed is:

1. A room temperature-curable storage stable organopolysiloxane composition which comprises, in admixture:
   (A) 100 parts by weight of an organopolysiloxane having a viscosity of at least 50 centipoise at 25° C. and at least two vinyl groups bonded to the silicon atoms in a molecule;
   (B) an organohydrogenpolysiloxane having at least three hydrogen atoms directly bonded to the silicon atoms in a molecule in an amount sufficient to provide from 0.5 to 4.0 moles of the silicon-bonded hydrogen atoms per mole of the vinyl groups bonded to the silicon atoms in the component (A);
   (C) a catalytic amount of a platinum compound;
   (D) from 20 to 600 parts by weight of an inorganic filler;
   (E) from 5 to 80 parts by weight of an aliphatic hydrocarbon compound which is liquid or semi-solid at room temperature; and
   (F) a compound selected from the group consisting of erythrobic acid, sodium erythorbate, 2,6-ditertbutyl p-cresol, tocopherol, butyl hydroxy anisole and propyl gallate, in an amount of at least 10 ppm by weight based on the aliphatic hydrocarbon compound as the component (E).

2. The room temperature-curable organopolysiloxane composition as claimed in claim 1 wherein at least 50% by moles of the organic groups bonded to the silicon atoms in the organopolysiloxane as the component (A) are methyl groups.

3. The room temperature-curable organopolysiloxane composition as claimed in claim 1 wherein the platinum compound as the component (C) is chloroplatinic acid.

4. The room temperature-curable organopolysiloxane composition as claimed in claim 1 wherein the amount of the platinum compound as the component (C) is in the range from 0.0001 to 0.1% by weight as platinum based on the total amount of the components (A) and (B).

5. The room temperature-curable organopolysiloxane composition as claimed in claim 1 wherein the aliphatic hydrocarbon compound which is liquid or semi-solid at room temperature has a viscosity of at least 50 centipoise at 25° C.

6. The room temperature-curable organopolysiloxane composition as claimed in claim 5 wherein the aliphatic hydrocarbon compound which is liquid or semi-solid at room temperature is liquid paraffin or petrolatum.

7. The room temperature-curable organopolysiloxane composition as claimed in claim 1 wherein the amount of the antioxidant as the component (F) is in the range from 100 to 5000 ppm by weight based on the amount of the aliphatic hydrocarbon compound as the component (E).

* * * * *